(12) United States Patent
Dabbs

(10) Patent No.: US 7,766,870 B2
(45) Date of Patent: Aug. 3, 2010

(54) FOLEY CATHETER ADAPTOR

(75) Inventor: Clifton R. Dabbs, Arlington, VA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 11/379,558

(22) Filed: Apr. 20, 2006

(65) Prior Publication Data
US 2008/0009793 A1    Jan. 10, 2008

Related U.S. Application Data

(60) Provisional application No. 60/673,388, filed on Apr. 21, 2005.

(51) Int. Cl.
*A61M 29/00* (2006.01)
(52) U.S. Cl. .................. 604/99.01; 604/98.02
(58) Field of Classification Search ... 604/96.01–99.04, 604/509, 533–537, 142, 185, 217
See application file for complete search history.

(56) References Cited

U.S. PATENT DOCUMENTS

| | | | | |
|---|---|---|---|---|
| 1,334,237 A | * | 3/1920 | Fleck | 604/99.02 |
| 3,356,093 A | * | 12/1967 | Monahon | 604/99.02 |
| 3,799,171 A | * | 3/1974 | Patel | 604/99.02 |
| 3,889,676 A | * | 6/1975 | Greene | 604/101.05 |
| 4,102,342 A | * | 7/1978 | Akiyama et al. | 606/192 |
| 4,147,170 A | * | 4/1979 | Taylor | 128/207.15 |
| 4,245,639 A | * | 1/1981 | La Rosa | 604/97.02 |
| 4,248,222 A | * | 2/1981 | Jaeger et al. | 128/207.15 |
| 4,335,723 A | | 6/1982 | Patel | |
| 4,598,707 A | * | 7/1986 | Agdanowski et al. | 128/207.15 |
| 4,813,935 A | * | 3/1989 | Haber et al. | 604/99.02 |
| 4,909,785 A | | 3/1990 | Burton et al. | |
| 4,968,298 A | * | 11/1990 | Michelson | 604/36 |
| 5,096,454 A | | 3/1992 | Samples | |
| 5,391,148 A | | 2/1995 | Bonis | |
| 6,102,929 A | * | 8/2000 | Conway et al. | 606/192 |
| 6,179,815 B1 | * | 1/2001 | Foote | 604/181 |
| 6,254,570 B1 | | 7/2001 | Rutner et al. | |
| 6,283,940 B1 | * | 9/2001 | Mulholland | 604/96.01 |
| 6,293,923 B1 | | 9/2001 | Yachia et al. | |
| 7,410,481 B1 | * | 8/2008 | Mitts et al. | 604/544 |

* cited by examiner

*Primary Examiner*—Matthew F Desanto
(74) *Attorney, Agent, or Firm*—Elizabeth Arwine

(57) ABSTRACT

A safety adaptor having attachment components and reservoir components for use with balloon anchored catheters such that if the catheter is forcibly removed the reservoir components will act as a safety valve and allow the anchoring balloon to deflate. The safety adaptor acts to minimize damage caused to a patient due to the removal of an inflated anchor balloon of a catheter. The safety adaptor attaches to any existing catheter having a fluid balloon and does not require re-engineering or re-tooling of the catheter or adaptor.

17 Claims, 5 Drawing Sheets

FOLEY CATHETER ADAPTOR

I. CROSS-REFERENCE TO RELATED APPLICATIONS

This application claims the benefit of U.S. Provisional Patent Application Ser. No. 60/673,388 filed Apr. 21, 2005, incorporated herein by reference.

II. FIELD OF THE INVENTION

The present invention relates to safety adaptors for use with catheters that have a balloon anchor.

III. BACKGROUND

The use of catheters to inject fluid into and drain fluid from a body cavity, vessel, canal, passage or duct of a patient is well-known. For urine drainage, the most commonly used catheter is the Foley catheter, named for its inventor. Certain patients may be catheterized with a Foley catheter to drain urine from the bladder through the urethra. In such a procedure, a catheter is inserted through the urethra until the distal end of the catheter is located in the bladder, after which a balloon adjacent the distal end of the catheter is inflated through an inflation lumen to retain the catheter in the patient. The proximal end of the catheter extends outside the patient's body and is usually connected to a drainage tube leading to a drainage bag. Urine passes through an opening or drainage eye adjacent the distal end of the catheter, through the drainage lumen extending through the catheter, and into the drainage tube to the bag for collection therein.

Foley catheters are generally sterile rubber or silicone tubing and are designed for insertion into the urethral meatus of the penis or vagina for the purpose of draining the urinary bladder. The Foley catheter is inserted until the catheter tip reaches the bladder and urine return is achieved. Once urine is draining through the tubing, sterile water, gas, or other fluid is pushed into a side port of another separate but attached tubing (or lumen) to inflate an external balloon proximate the tip of the catheter inside the bladder to anchor the catheter in the bladder. Currently there is no way of deflating the balloon, except by manually connecting a syringe to the port and removing the fluid.

Anchoring the catheter insures that the device stays in place while performing the desired function and it is also helpful in preventing intentional and/or accidental removal of the catheter. While anchoring the catheter is helpful in preventing its removal, removals do still occur. The removal of anchored catheters presents a serious risk of injury to patients.

An enormous number of urinary catheters are used daily in the United States. It is estimated that approximately 10 to 15 percent of patients admitted to the hospital receive a Foley catheter. Currently, if the balloon affixed to the Foley catheter is manually extracted while inflated, the balloon often tears the urethral mucosa causing strictures (scarring), bleeding, and infections. There have been numerous occasions when patients have self-extracted their catheters with the balloon fully inflated. Significant damage occurs to the urinary tract when such events occur.

A need exists for a safety device that attaches to a catheter that allows for the rapid release of pressure in the anchoring or attachment structures in order to minimize the risk of injury to patients when the catheters are forcibly removed.

IV. SUMMARY OF THE INVENTION

In an exemplary embodiment, the present invention provides an adaptor for use with a balloon anchored catheter, including a tube, a reservoir connected to the tube, an expandable reservoir member connected to the reservoir, and an attachment structure connected to the tube.

In another exemplary embodiment, the present invention provides a catheter system including a main catheter including a main flow tube; an anchoring catheter connected to the main catheter, the anchoring catheter comprising a port, an anchoring flow tube and an anchoring structure; and, an adaptor connected to the anchoring catheter, the adaptor comprising a tube structure; a reservoir connected to the tube structure; an expandable reservoir member connected to the reservoir; and, an attachment structure connected to the tube structure.

In still another exemplary embodiment, the present invention provides a catheter system including a main catheter including a main flow tube; an anchoring catheter connected to the main catheter, the anchoring catheter comprising a port, an anchoring flow tube, and an anchoring structure; and, an adaptor connected to the anchoring catheter, wherein the adaptor acts to minimize damage to a patient due to the removal of the main catheter or the anchoring catheter.

In yet another exemplary embodiment, the present invention provides an adaptor for use with a balloon anchored catheter, the adaptor including means for providing a balloon anchored catheter; and, means for providing a safety valve that allows release of pressure at an anchor balloon site of the catheter when the catheter is removed.

An attachment structure attaches the safety adaptor to a balloon anchored catheter and the adaptor acts to minimize damage to a patient due to the forcible removal of the balloon anchored catheter. The adaptor minimizes damage by rapidly allowing fluid from an anchor balloon of the balloon anchored catheter to enter the reservoir thereby relieving pressure at the anchor balloon site. This rapid release of pressure from the anchor balloon occurs when the force applied to the anchor balloon overcomes the surface tension of a flexible membrane in the adaptor.

The safety adaptor in at least one exemplary embodiment is a medical device that is attached securely to the input/output port of the anchoring balloon of a catheter. The adaptor is a safety device that allows the anchoring balloon to rapidly release itself once a certain amount of force is exerted on the balloon. The adaptor greatly reduces the trauma associated with balloon anchored catheter self extractions.

V. BRIEF DESCRIPTION OF THE DRAWINGS

The present invention is described with reference to the accompanying drawings, wherein.

Given the following enabling description of the drawings, the apparatus and methods should become evident to a person of ordinary skill in the art.

VI. DETAILED DESCRIPTION OF THE INVENTION

The present invention describes an apparatus and method providing a safety adaptor for use with a catheter. The safety adaptor of the present invention allows a catheter to be forcibly removed without causing great trauma to the body. The adaptor acts to rapidly release pressure from an anchor balloon of a balloon anchored catheter when the force applied to the anchor balloon overcomes the surface tension of a flexible membrane of the adaptor.

Figure 1A:
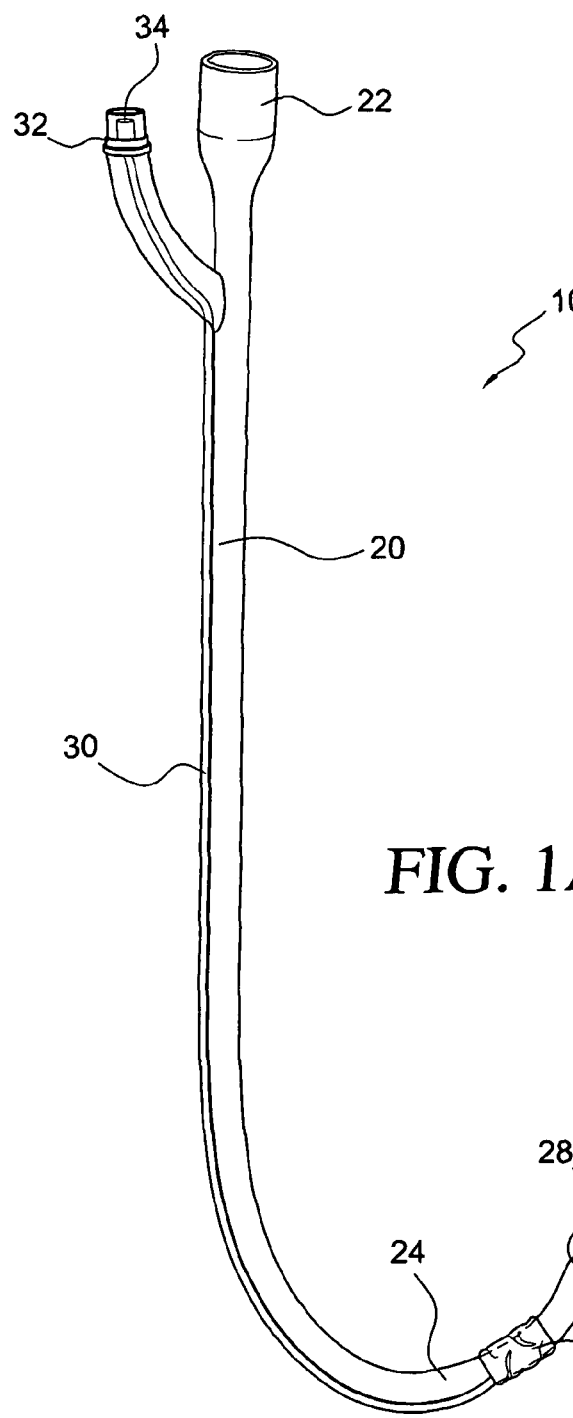
FIG. 1A illustrates a Foley catheter and bladder anchoring balloon structure.
Figure 1B:
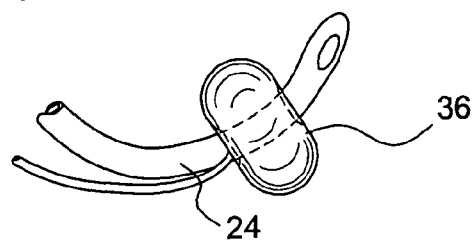
FIG. 1B illustrates a cut away view of the anchoring balloon structure, as illustrated in FIG. 1A.

With reference to the drawings, FIGS. 1A and 1B show a balloon anchored catheter 10 such as a Foley catheter that is insertable into a body cavity, vessel, canal, passage or duct to inject or drain fluid into or from the body. One exemplary use of the catheter 10 is to drain urine from a patient's bladder and/or to inject fluid into the patient's bladder.

In order to facilitate insertion into the body, the catheter 10 includes a long, slender, and flexible sterile flow tube 20 having a distal end 24 and a proximal end 22. The distal end 24 has a thin tip 26 that includes an opening 28. The flow tube 20 has attached to it a separate anchor tube 30 that extends along the length of the flow tube 20 from the distal end 24 to the proximate end 22. The anchor tube 30 ends in a fluid intake/output port 32 at the proximal end. The anchor tube 30 is also fluidly connected to an anchor balloon 36 that surrounds the distal end 24 of the catheter tip 26.

The catheter tip 26 and anchor balloon 36 are inserted into the bladder while the anchor balloon 36 is deflated. Once the catheter tip 26 and anchor balloon 36 are inside the bladder a fluid is injected through the anchor tube 30 into the anchor balloon 36. This fluid inflates the anchor balloon 36 such that the diameter of the anchor balloon 36 exceeds the diameter of the urethra thereby securing the distal end 24 of the flow tube 20 including the catheter tip 26 inside the bladder.

The inflation of the anchor balloon 36 is achieved by attaching a fluid source (not shown) to the fluid intake/output port 32 of the anchor tube 30. The fluid source may be, for example, a syringe that attaches to a one-way valve 34 found in the fluid intake/output port 32. When the syringe is attached to the intake/output port 32, the one-way valve 34 is depressed and opened allowing fluid to pass into the anchor tube 30. A sufficient amount of fluid is then injected into the anchor tube 30 to inflate the anchor balloon 36.

Once the anchor balloon 36 is sufficiently inflated, the fluid source is disengaged from the input/output port 32 thereby closing the valve 34. Once the valve 34 is closed, there exists a closed fluid system from the anchor balloon 36 through the anchor tube 30 and to the valve 34 of the fluid intake/output port 32. This closed fluid system presents a potential risk of injury to the patient's bladder and/or urethra resulting from the removal of the catheter 10 and inflated anchor balloon 36.

The removal of the catheter 10 while the anchor balloon is inflated can be intentional or accidental. Generally, the only means for removing fluid from the anchor balloon 36 is by withdrawing the fluid, for example, with a syringe attached to the input/output port 32. However, patient's often attempt to remove the catheter 10 themselves while the anchor balloon 36 is inflated. While at other times, accidental mishaps, such as the tubing 20, 30 becoming entangled or snagged can lead to the catheter 10 being traumatically removed. Both of these occurrences present a substantial risk of injury. These injuries include bleeding, scarring, strictures, rupture of the urethra, rupture of the balloon and contamination due to balloon fragments, etc.

Figure 2A:
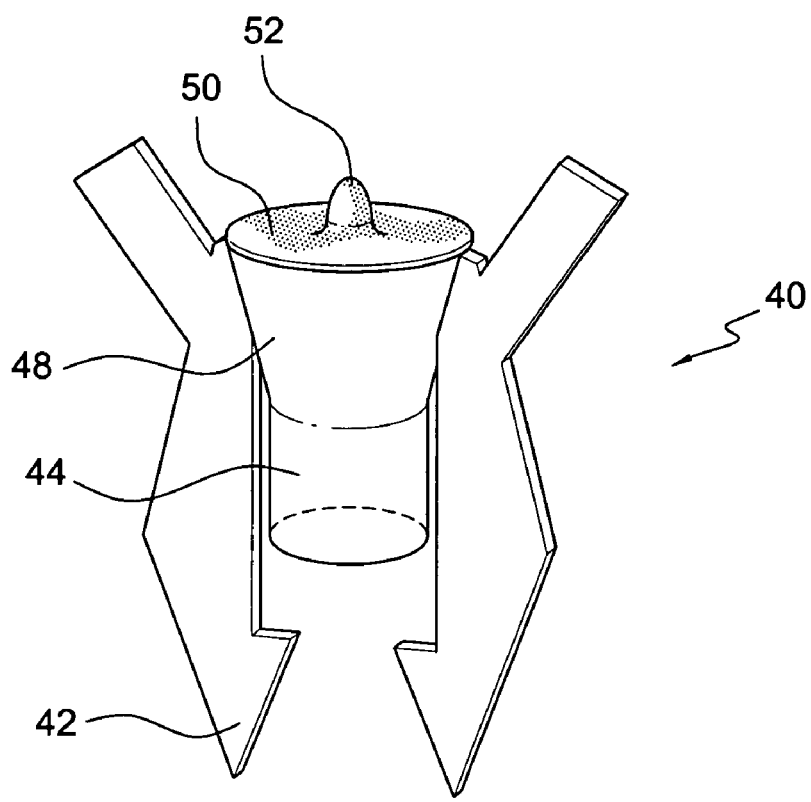
FIG. 2A illustrates a perspective view of an exemplary embodiment of the adaptor of the present invention.
Figure 4:
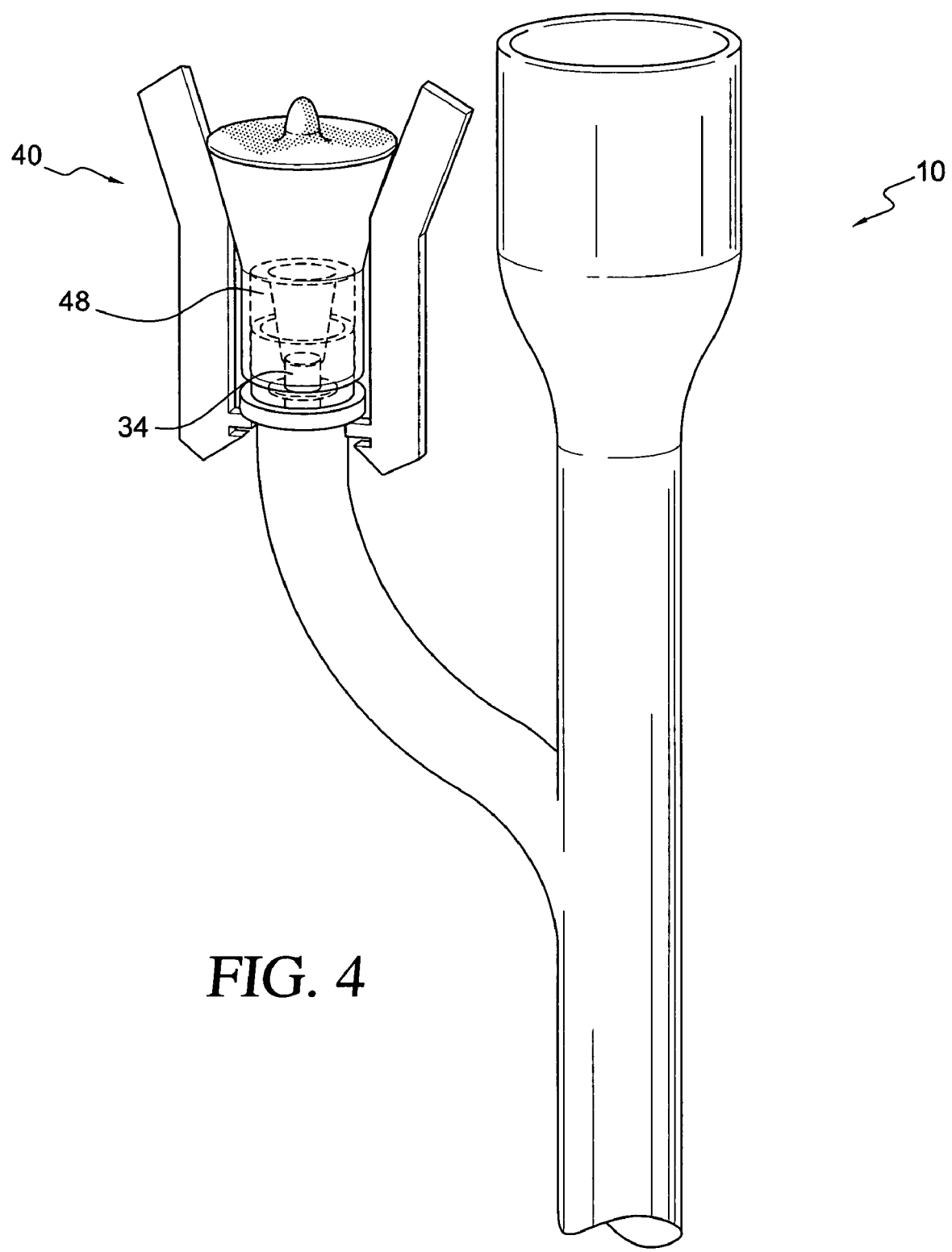
FIG. 4 depicts an exemplary embodiment of the balloon anchored catheter and adaptor according to the present invention.

In order to minimize the risk of injury, the present invention in one exemplary embodiment, as illustrated in FIG. 2A, provides a catheter adaptor 40 that acts to release the fluid pressure in the closed fluid system by allowing the inflated anchor balloon 36 to be removed without causing serious injury to the bladder or urethra. In one exemplary embodiment, the catheter adaptor 40 includes an adaptor attachment structure 42 that attaches the adaptor 40 to the fluid intake/output port 32 of the anchor tube 30, as illustrated in FIG. 4. The adaptor attachment structure 42 allows the adaptor 40 to be attached to most any currently existing catheter without the need for re-engineering or retooling of the catheter or adaptor 40.

Figures 2B, 2C:
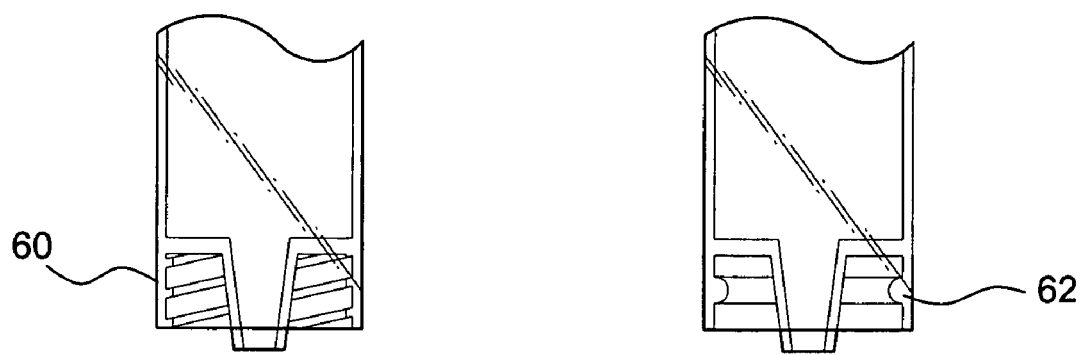
FIG. 2B depicts a partial side view of an exemplary embodiment of an attachment structure according to the present invention.
FIG. 2C depicts a partial side view of an exemplary embodiment of an attachment structure according to the present invention.

In keeping with the spirit of the present invention, the adaptor attachment structure 42 may assume various embodiments for attachment to the outside of the valve housing, including, for example, clothespin, locking arms, clamps, or clasps type fasteners, similar to the fastener illustrated in FIG. 2A. The attachment structure 42 illustrated in FIG. 2A includes a pair of pinch members that hook around a ridge (or other protrusion) commonly found on the fluid intake/output port of a catheter balloon lumen. This structure also allows for a pinching force to be applied if no ridge is present. The pinch members flex to open sufficiently to hook the ridge and/or to clamp the fluid intake/output port. The attachment structure may also assume embodiments including, for example, a Luer lock having threads 60, as illustrated in FIG. 2B, or frictional fasteners such as an O-ring 62, as shown illustrated in FIG. 2C. The various attachment structures are examples of means for connecting to a balloon anchor valve.

Figure 3A:
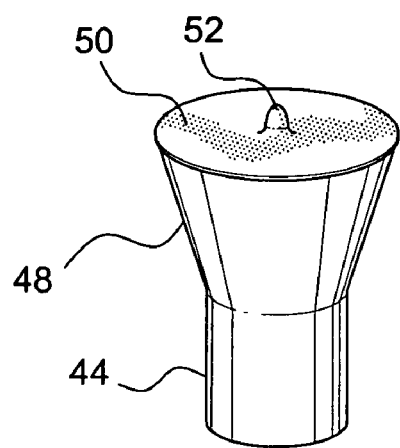
FIG. 3A illustrates a perspective view of an exemplary embodiment of the reservoir according to the present invention.
Figure 3B:
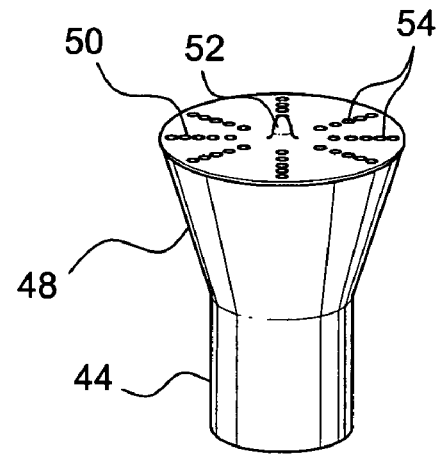
FIG. 3B illustrates a perspective view of another exemplary embodiment of the reservoir according to the present invention.

The adaptor attachment structure 42 is connected to a fluid reservoir 48 that has an open end. The open end of the fluid reservoir 48 is configured to engage the fluid intake/output port 32 of the catheter 10. As illustrated in FIGS. 2A and 3A, the fluid reservoir 48 includes a cylindrical member (or sleeve) 44 at the open end with the top region flaring out from the cylindrical member 44. As illustrated in FIG. 3D, the fluid reservoir 48 may be just a cylindrical member. A variety of shapes can be utilized for the fluid reservoir 48 while allowing it to open the fluid intake/output port 32 and establish fluid communication. The fluid reservoir 48 includes a tension membrane (or elastic member) 50 on the end opposite the cylindrical member 44. The tension membrane 50 as illustrated includes an expandable nipple 52, which can take a variety of shapes while providing sufficient expansion area for receiving fluid. The tension membrane 50 and the fluid reservoir 48 together are an exemplary means for receiving fluid released from an anchor balloon of a balloon anchored catheter during force removal.

Figure 3C:
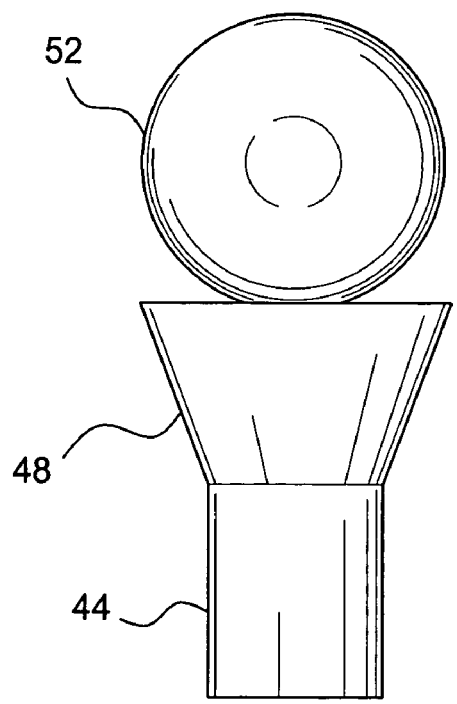
FIG. 3C illustrates a side view of an exemplary embodiment of the reservoir according to the present invention.
Figure 3D:
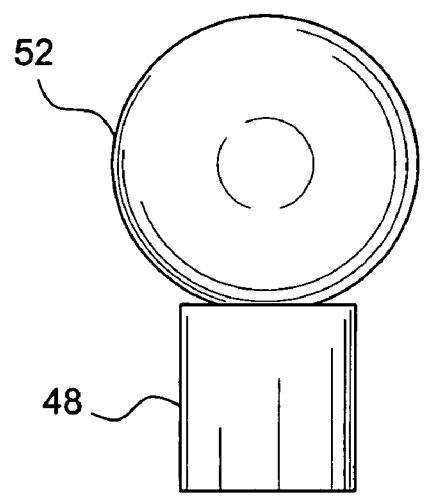
FIG. 3D illustrates a side view of another exemplary embodiment of the reservoir according to the present invention.

The expandable nipple 52 expands, as illustrated in FIGS. 3C and 3D to accommodate fluid that enters the reservoir 48 from the anchor balloon 36 and anchor tube 30 when sufficient pressure is exerted onto the anchor balloon 36, for instance during the forcible removal of the catheter 10 while the anchor balloon 36 is inflated. The tension membrane 50 and/or expandable nipple 52 may be, for example, a thin elastic membrane of rubber, polymer or latex that expands or bursts in order to relieve pressure from the anchor balloon 36.

In one embodiment, the tension membrane 50 has a surface tension selected to be higher than the surface tension of the anchor balloon 36. This surface tension of the tension membrane 50 acts under normal system pressures to prevent fluid from entering and expanding the cavity formed by the tension membrane 50 and the fluid reservoir 48 such that the anchor balloon 36 remains inflated. The surface tension of the expandable nipple 52 is selected to be lower than the surface tension of the tension membrane 50. The selected surface tension allows the expandable nipple 52 to stretch in order to accept at least the amount of fluid displaced from the anchor balloon 36 and anchor tube 30 when forces act on the anchor balloon 36 such as when the catheter 10 and anchor balloon 36 are forcibly removed.

In another exemplary embodiment, the expandable nipple 52 may alternatively be selected to have properties such that the nipple 52 bursts when a certain amount of fluid is displaced from the anchor balloon 36 and anchor tube 30 into the reservoir 48 when the catheter 10 and anchor balloon 36 are forcibly removed. The tension membrane 50 and/or the expandable nipple 52 may be designed to suit a variety of conditions. For example, the tension membrane 50 and/or the expandable nipple 52 may be designed to exhibit a weakened surface tension that allows the tension membrane 50 and/or the expandable nipple 52 to expand very easily. The tension membrane 50 and/or the nipple 52 may also be designed to have partial perforations or faults 54, as illustrated in FIG. 3B. The faults 54 facilitate bursting and release of the anchoring fluid under a certain amount of pressure.

Figure 5:
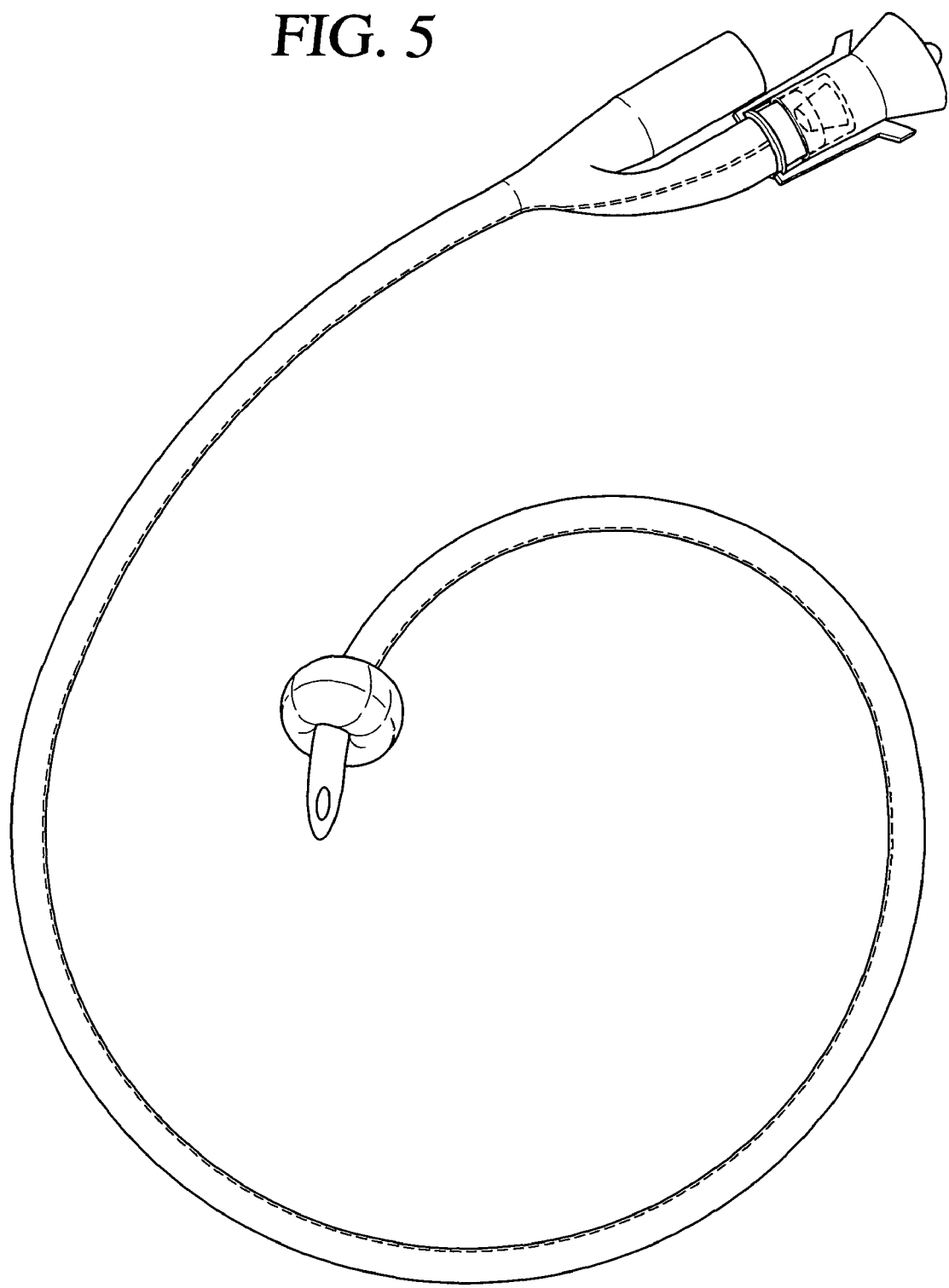
FIG. 5 depicts an exemplary embodiment of the balloon anchored catheter and adaptor according to the present invention.

When the adaptor 40 is attached to the catheter 10, as illustrated in FIG. 4 and 5, the fluid reservoir 48 depresses and opens the valve 34 of the fluid intake/output port 32. The fluid reservoir 48 comprises a male fitting that locks in a female portion of the fluid intake/output port 32 that when in place fully depresses the valve 34 of the intake/output port 32. The fluid reservoir 48 including allows a small amount of fluid from the closed fluid system to enter into the tube 44 of the adaptor 40.

Fluid in the anchor balloon 36 will not be able to escape due to the tension membrane 50 with expandable nipple 52. However, when sufficient pressure is placed on the anchor balloon 36 inside the urinary bladder (such as when the patient pulls forcefully on the catheter trying to self extract the catheter 10) the pressure placed on the anchor balloon 36 will overcome the tension membrane 50 of the adaptor 40 and the fluid will displace from the anchor balloon 36 so that the catheter 10 slides out with significantly less trauma to the bladder and urethra.

In practice, when the inflated anchor balloon 36 is attempted to be pulled into the urethra from the bladder, the urethral wall exerts a certain amount of tension on the anchor balloon 36. This tension causes circumferential pressure on the anchor balloon 36 so that the fluid pressure overcomes the surface tension of the rubber tension member 50 in the adaptor 40. This causes fluid to be displaced to the tension membrane 50 and expandable nipple 52 such that the catheter 10 easily slides out of the bladder.

The foregoing has outlined a safety adaptor for a balloon anchored catheter that acts to minimize damage to a patient due to the forcible removal of the balloon anchored catheter. The adaptor minimizes damage by rapidly allowing fluid from an anchor balloon of the balloon anchored catheter to enter a reservoir and thereby relieve pressure at the anchor balloon site.

The adaptor of the present invention is a medical device that attaches securely to an input/output port of the bladder anchoring balloon of a catheter. The adaptor, in at least one exemplary embodiment, includes an attachment structure that allows the adaptor to be used with most any currently existing catheter, particularly Foley catheters, and greatly reduces the trauma associated with catheter self extractions.

Although the present invention has been described in terms of particular embodiments, it is not limited to those embodiments. Alternative embodiments, examples, and modifications which would still be encompassed by the invention may be made by those skilled in the art, particularly in light of the foregoing teachings.

Those skilled in the art will appreciate that various adaptations and modifications of the embodiments described above can be configured without departing from the scope and spirit of the invention. Therefore, it is to be understood that, within the scope of the appended claims, the invention may be practiced other than as specifically described herein.

I claim:

1. A catheter system comprising:
   a main catheter including a passageway;
   an anchoring catheter connected to said main catheter, said anchoring catheter comprising:
      a fluid port containing a one-way valve,
      an anchoring flow tube connected to said fluid port, and
      an anchoring structure connected to a distal end of said anchoring flow tube; and
   an adaptor connected to said anchoring catheter, said adaptor comprising:
      a fluid reservoir;
      an attachment structure connected to said fluid reservoir, wherein said attachment structure attaches said adaptor in fluid communication with said anchoring structure;
      an elastic member connected to and enclosing a distal end of said reservoir, wherein said elastic member includes an expandable nipple that receives fluid displaced from said anchoring structure; and
      a cylindrical sleeve member connected to a proximal end of said fluid reservoir, wherein said cylindrical sleeve member depresses and opens said one-way valve creating an open fluid pathway between said anchoring structure and said fluid reservoir.

2. A catheter system according to claim 1, wherein said elastic member is made of a material that expands to receive fluid displaced from said anchoring structure.

3. A catheter system according to claim 1, wherein said elastic member includes an expandable nipple.

4. A catheter system according to claim 1, wherein said elastic member is made of a material that bursts when fluid is received from said anchoring structure.

5. A catheter system according to claim 1, wherein said elastic member includes a perforated membrane, wherein said perforated membrane bursts when a volume of fluid is displaced into said elastic member.

6. A catheter system according to claim 1, further comprising an attachment structure that connects said adaptor to said anchoring structure.

7. An adaptor for use with a balloon anchored catheter having a one-way valve, said adaptor comprising:
- a fluid reservoir;
- an attachment structure connected to said fluid reservoir, wherein said attachment structure attaches said adaptor in fluid communication with an anchoring structure of a balloon anchored catheter;
- an elastic member connected to and enclosing a distal end of said fluid reservoir, wherein said elastic member includes an expandable nipple that receives fluid displaced from said anchoring structure; and
- a cylindrical sleeve member connected to a proximal end of said reservoir, wherein said cylindrical sleeve member depresses and opens a one-way valve of said balloon anchored catheter such that fluid is displaced from said anchoring structure and into said adaptor when pressure is exerted onto said anchoring structure.

8. An adaptor according to claim 7, wherein said elastic member includes perforations.

9. An adaptor according to claim 8, wherein said elastic member bursts when a volume of fluid is displaced into said elastic member.

10. An adaptor according to claim 7, wherein said elastic member is connected to one end of said cylindrical sleeve member and the other end of said cylindrical sleeve member engages the one-way valve of said balloon anchored catheter.

11. An adaptor according to claim 7, wherein said adaptor receives fluid displaced from said anchoring structure when pressure is exerted onto said anchoring structure.

12. An adaptor according to claim 7, wherein said expandable nipple is capable of expanding at least to accommodate a volume equal to the volume of fluid in said anchoring structure.

13. An adaptor according to claim 7, wherein said elastic member is made of a material that bursts in response to receiving fluid from said anchoring structure.

14. An adaptor according to claim 7, wherein said attachment structure comprises locking arms, clamps, or clasps.

15. An adaptor according to claim 7, wherein said attachment structure comprises a Luer lock or an O-ring.

16. An adaptor for use with a balloon anchored catheter, said adaptor comprising:
- means for connecting the adaptor to a fluid port of a balloon anchored catheter, wherein said fluid port includes a one-way valve;
- means for depressing and opening said one-way valve when said adaptor is connected to said fluid port; and
- means for receiving fluid released from an anchor balloon of said balloon anchored catheter during forced removal, wherein said means for receiving fluid includes an elastic membrane having a nipple that expands to contain at least a portion of the received fluid.

17. An adaptor according to claim 16, wherein said means for receiving fluid includes means for releasing pressure on said elastic membrane.

* * * * *